United States Patent [19]
Roth et al.

[11] Patent Number: 6,086,948
[45] Date of Patent: Jul. 11, 2000

[54] PROCESS FOR MANUFACTURING CERAMIC, DIFFUSION-LIMITING LAYERS AND USE OF THESE LAYERS

[75] Inventors: Barbara Roth; Volker Brüser; Ulrich Guth, all of Greifswald, Germany

[73] Assignee: Heraeus Electro-Nite International N.V., Houthalen, Belgium

[21] Appl. No.: 09/313,941

[22] Filed: May 19, 1999

[30] Foreign Application Priority Data

Jun. 5, 1998 [DE] Germany ............... 198 25 094

[51] Int. Cl.⁷ ............... B05D 1/12; B05D 1/32; B05D 5/12
[52] U.S. Cl. ............... 427/126.2; 427/126.3; 427/126.4; 427/201; 427/282; 427/376.2
[58] Field of Search ............... 427/126.2, 126.3, 427/126.4, 190, 201, 282, 376.2; 204/429; 501/80; 264/628

[56] References Cited

U.S. PATENT DOCUMENTS

| | | |
|---|---|---|
| 4,421,787 | 12/1983 | Ikezawa et al. . |
| 4,957,673 | 9/1990 | Schroeder et al. . |
| 5,122,487 | 6/1992 | Hayakawa et al. . |
| 5,310,575 | 5/1994 | Friese et al. . |
| 5,522,979 | 6/1996 | Tatumoto et al. . |

FOREIGN PATENT DOCUMENTS

| | | |
|---|---|---|
| 0 334 727 A1 | 9/1989 | European Pat. Off. . |
| 0 395 925 A1 | 11/1990 | European Pat. Off. . |
| 29 45 020 A1 | 5/1981 | Germany . |
| 42 31 966 A1 | 3/1994 | Germany . |
| 43 43 315 A1 | 6/1995 | Germany . |
| 41 43 539 C2 | 9/1996 | Germany . |

*Primary Examiner*—Fred J. Parker
*Attorney, Agent, or Firm*—Akin, Gump, Strauss, Hauer & Feld, L.L.P.

[57] ABSTRACT

Porous, ceramic layers, which also have a diffusion-limiting action, are as a rule manufactured by selectively adding pore formers to the ceramic sinter material. The porosity of the layer created in this way lies in the micrometer range. The known processes for manufacturing layers of this type are intended for application to planar substrates. Suitability for spherical surfaces and a porosity of the layer in the nanometer range is provided herein by an oxide ceramic powder having a BET specific surface area in the range of about 5 to 50 $m^2/g$ and having a mean primary particle size of about 20 to 450 nm. The powder is first pretreated at a temperature of about 800° C. to 1150° C. and then mixed with untreated, oxide ceramic powder. The mixture is then applied to a high temperature-stable base, and burned-in (fired) at a temperatures of about 1000° C. to 1350° C. Optionally, instead of the thermally pretreated oxide ceramic powder, a recrystallized glass powder can be used. The firing temperature range in this case, however, is about 850° C. to 1000° C.

9 Claims, No Drawings

PROCESS FOR MANUFACTURING CERAMIC, DIFFUSION-LIMITING LAYERS AND USE OF THESE LAYERS

BACKGROUND OF THE INVENTION

The invention relates to a process for manufacturing ceramic, diffusion-limiting layers using finely dispersed, ceramic powder, as well as to use of the layer.

A porous $ZrO_2$ ceramic is known, for example, from German published patent application DE 29 45 020 A1, whose porosity or gas permeability is regulated by the addition of $TiO_2$ to $ZrO_2$. The porosity increases with increasing $TiO_2$ content. For establishing the porosity, a briquette made of a powder mixture of $ZrO_2$ (fully stabilized) and $TiO_2$ is produced which, following sintering at 1470° C., has a gas permeability of about $10^{-5}$ to $10^{-3}$ bar ml/sec $cm^2$. It is further disclosed in DE 29 45 020 that a porous molded element, for example as a platelet, is mounted on an electrode of an electrochemical measuring sensor and consequently serves as a porous protective layer. For fastening such a platelet on a measuring sensor a glazing is suggested.

Furthermore, German published patent application DE 42 31 966 A1 describes a porous ceramic layer as a diffusion barrier or as a diffusion channel. Here as well, the layer consists of $ZrO_2$, wherein the porosity of the diffusion layer is created by the addition of pore-forming materials, as for example thermal carbon black, theobromine or indanthrene blue, which burn, decompose or vaporize during the sintering process. The amounts of such pore-forming materials added in accordance with DE 42 31 966 is relatively high, so that a porosity of 10 to 50% is created with a mean pore diameter between 5 and 50 $\mu$m. The $ZrO_2$ powder and the pore-forming materials are brought into contact with organic binding agents and solvents, so that a ceramic green sheet can be produced from this, which is processed further in the socalled tape technology. Glass carbon is also mentioned in German published patent application DE 43 43 315 A1 as an additional pore-forming material, which is here further processed, likewise with a ceramic powder, into a tape or a paste. Depending on the grain diameter of the glass carbon, pore sizes between 1 and 150 $\mu$m are attained following the sintering of the material according to DE 43 43 315.

The disadvantages of these possibilities of manufacturing porous ceramic layers according to the cited prior art lie in that the pore or pore channel diameters are relatively large for the use as gas permeable layers in gas sensors, whereby the danger exists of becoming stopped up by particles from the combustion gas stream, with the consequence of a short lifetime of sensors of this type. Moreover, for tube-shaped sensors the tape technology disclosed in DE 42 31 966 and DE 43 43 315 is not especially suited, since the usual lamination is more suited for planar and not for spherical surfaces.

SUMMARY OF THE INVENTION

It is therefore an object of the invention to overcome the above described disadvantages of the prior art, and thereby to provide a process which permits manufacturing a porous ceramic layer with a porosity in the nanometer range (approximately 70 nm to 600 nm) and which is moreover suited for layers on planar as well as on spherical molded elements.

The foregoing object is solved in accordance with the invention, in that an oxide ceramic powder is used which has a specific surface area according to BET (Brunauer, Emmett and Teller) in the range of 5 to 50 $m^2/g$ and a mean primary particle size of 20 to 450 nm, wherein first of all a portion of the powder is thermally pretreated at a temperature of 800° C. to 1150° C. and is then mixed with the untreated portion of the oxide ceramic powder, in order subsequently to be applied on a high temperature-stable base and burned-in (fired) at temperatures of 1000° C. to 1350° C.

Through the thermal pretreatment of a portion of the finely dispersed, oxide ceramic powder, its sintering activity is reduced. The tempering of the powder corresponds to a presintering. This thus-adjusted powder mixture and the screen printed layer produced therefrom permit a sintering sequence adapted to the high temperature-stable base (preferably a substrate of an oxygen ion-conducting solid electrolyte), which as a result leads to a homogenous, firmly adhering layer with designed nano-scale porosity. The powder mixture of untreated, oxide ceramic and thermally pretreated, oxide ceramic powder or the porous layer manufactured by the process of the invention acts (so far as, for example, completely stabilized $ZrO_2$ is used, which at higher temperatures manifests quite a significant oxygen ion conductivity) as a gas-limiting diffusion layer, for example on a pump electrode of a polarographic oxygen sensor, and optionally also as a solid electrolyte.

Alternatively, the objective of the invention is accomplished in that an oxide ceramic powder, which has a specific surface area according to BET (Brunauer, Emmett and Teller) in the range of 5 to 50 $m^2/g$ and a mean primary particle size of 20 to 450 nm, is mixed with a recrystallized glass powder from a $SiO_2$-$Al_2O_3$-BaO system, in order subsequently to be applied to a high temperature-stable base and burned-in at temperatures of 850° C. to 1000° C.

The addition of the recrystallized glass powder acts so that no fluid melt forms at temperatures of 850° C. to 1000° C., but instead an adhesion of the oxide powder particles occurs, which likewise leads to a nano-scale porosity. The ceramic powder has as typical powder characteristic values a BET specific surface area of 5 to 50 $m^2/g$ and a mean primary particle size of 20 to 450 nm. The combination of an oxide ceramic powder with a recrystallized glass powder leads to a porous layer which is also suited for operating temperatures up to 800° C. In the burned-in layer, a distinct separation between glass phase and powder phase forms, which is brought about through the difference between the specific densities of the recrystallized glass with about 3.1 $g/cm^3$ and the oxide powder, for example of $ZrO_2$, with a density of about 6.0 $g/cm^3$. The separation of the material phase takes place in such a manner that, by arrangement of the layer of the invention as cover layer on an electrode, the oxide powder particles are enriched in the direction of the electrode, and an increase of the gas phase proportion is to be observed in the direction of the outer environment or the gas space. Sensors with ceramic cover layers of this type show little or no temperature dependency of the sensor signal.

DETAILED DESCRIPTION OF THE INVENTION

Advantageous configurations and refinements of the process of the invention are described below and in the dependent claims. According to a preferred embodiment of the invention, a partially or completely stabilized $ZrO_2$ powder or an $Al_2O_3$ powder or mixtures thereof (which manifest oxygen ion conductivity at higher temperatures) are used for the finely dispersed powder. The complete stabilization of the $ZrO_2$ powder can take place, for example, by administration of 8 mol percent of $Y_2O_3$.

The chemical composition of the recrystallized glass powder preferably lies in the range of 35–51 weight percent $SiO_2$, 25–38 weight percent $Al_2O_3$, and 10–39 weight percent BaO, wherein further small additions of alkaline earth oxides, such as CaO or MgO can be advantageous.

If the finely dispersed, oxide ceramic powder is mixed with a recrystallized glass powder or with the thermally pretreated powder, the proportions of the untreated powder in relation to the thermally treated powder or the recrystallized glass powder lie in the range of 10% by weight to 50% by weight.

Advantageously, the powder mixture is processed into a paste with the help of working-up agents, for example an ethyl cellulose solution, which is applied to a base in a screen printing process. A planar or spherical substrate, for example of fully stabilized $ZrO_2$, can be used as the base. This base can be coated on both sides with a functional layer in the form of congruently-lying electrodes. Furthermore, one of the electrodes therein can be completely covered by a diffusion-limiting layer of the invention.

In the case of the ceramic layer with the properties of diffusion-limiting and oxygen ion-conducting, an electrode layer is applied on one side of a planar or spherical ceramic base. The diffusion-limiting and oxygen ion-conducting layer follows on this electrode, which is once again covered by a second electrode layer.

By the sintering of the applied layer in the temperature range of 850° C. to 1000° C., to the extent that recrystallized glass is contained in it, or in the temperature range of 1000° C. to 1350° C., to the extent only oxide ceramic material is used, a porous ceramic layer with a layer thickness in the range of 15 to 100 $\mu$m arises. In order to obtain information about the porosity of the layer or its effectiveness in relation to its diffusion-limiting property, a raster electron microscopic scan and/or a so-called helium leakage rate test can be employed, for example. With the leakage rate test, a defined surface segment of the porous layer is exposed to a helium atmosphere on a gas-tight carrier material, and the pressure loss, which results from the helium diffusing through the layer, is measured. The permeability in relation to helium is substantially higher in comparison to that in relation to oxygen, owing to the different molecule size, so that in practice with the described leakage rate test, only a relative value in relation to the diffusion-limiting property of the layer results with respect to oxygen. Together with a raster electron microscopic scan, however, an absolute statement can be made about the quality of the layer produced according to the process of the invention.

The layers manufactured according to the above-mentioned process can be used as a diffusion layer and/or as an oxygen ion-conducting layer with oxygen probes for determining the oxygen in gases. The invention will now be illustrated in more detail with reference to the specific examples below.

EXAMPLE 1

A $ZrO_2$ powder completely stabilized with 8 mol percent of $Y_2O_3$ (hereinafter "8YSZ-powder") is used as the oxide ceramic powder. It has a BET specific surface area of 13.2 $m^2/g$. The mean primary particle size of the essentially spherical powder particles amounts to 240 nm. Half of the powder is thermally pretreated for 10 hours at 1150° C., in order to be mixed subsequently with the untreated half of the powder. This powder mixture forms the solid component of a paste, which is produced by adding a screen printing medium, for example ethyl cellulose dissolved in terpineol.

The paste is applied in a screen printing process to a substrate with sintered electrodes or other functional layers, dried and fired for two hours at a maximum temperature of 1300° C.

EXAMPLE 2

30 parts by weight of an 8YSZ powder (see Example 1) with a BET specific surface area of 30 $m^2/g$ and a mean primary particle size of 90 nm are pretreated for 5 hours at 800° C. and then mixed with 70 parts by weight of the previously mentioned, untreated 8YSZ powder. From this mixture a paste is produced according to the procedures of Example 1, and is applied to a functional layer, for example an electrode, in a screen printing process. The firing here takes place for 2 hours at 1150° C.

EXAMPLE 3

50 parts by weight of an 8YSZ powder with a BET specific surface area of 5.5 $m^2/g$ and a mean primary particle size of 430 nm are mixed with 50 parts by weight of a recrystallized glass powder having a composition of 35.0 weight percent $SiO_2$, 26.3 weight percent $Al_2O_3$, 29.4 weight percent BaO, 5.2 weight percent CaO, and 4.1 weight percent MgO, wherein the glass powder has a BET specific surface area of 3.5 $m^2/g$. From this mixture a paste is produced according to the procedures in accordance with Example 1, and is applied in a screen printing process to a substrate or to a functional layer, for example an electrode. The firing takes place here for 0.5 hours at 1000° C.

The layers created in accordance with Examples 1 and 2 represent double functional layers, in that, on the one hand, they can assume the function of a diffusion-limiting cover layer and, on the other hand, they can assume the function of an oxygen ion conductor. The layer in accordance with Example 3, in contrast, has exclusively diffusion-limiting characteristics, owing to the low proportion of the YSZ powder.

It will be appreciated by those skilled in the art that changes could be made to the embodiment(s) described above without deportioning from the broad inventive concept thereof. It is understood, therefore, that this invention is not limited to the portionicular embodiment(s) disclosed, but it is intended to cover modifications within the spirit and scope of the present invention as defined by the appended claims.

We claim:

1. A process for manufacturing a ceramic, diffusion-limiting layer using finely dispersed, ceramic powders, comprising providing an oxide ceramic powder having a BET specific surface area in a range of 5 to 50 $m^2/g$ and a mean primary particle size of 20 to 450 nm, thermally pretreating a first portion of the powder at a temperature of about 800° C. to 1150° C. for a time sufficient to reduce its sintering activity, mixing the thermally pretreated powder first portion with the untreated portion of the powder, applying a layer of the mixed powder to a thermally-stable base, and firing the powder-coated base at a temperature in a range of about 1000° C. to 1350° C. to form the ceramic layer.

2. The process according to claim 1, wherein the oxide ceramic powder is selected from the group consisting of an at least partially stabilized $ZrO_2$, an $Al_2O_3$ powder, and mixtures thereof.

3. The process according to claim 1, wherein the untreated, oxide ceramic powder is mixed with the thermally pretreated powder in a proportion of about 10% by weight to 50% by weight of the thermally pretreated powder.

4. The process according to claim 1, wherein said ceramic, diffuision-limiting layer forms a diffusion layer and/or oxygen ion-conducting layer in an oxygen probe for determining oxygen in gases.

5. A process for manufacturing a ceramic, diffusion-limiting layer, comprising mixing a finely dispersed oxide ceramic powder having a BET specific surface area in a range of about 5 to 50 $m^2/g$ and a mean primary particle size of about 20 to 450 nm with a recrystallized glass powder of a $SiO_2$-$Al_2O_3$-BaO system, applying the mixture to a thermally-stable base, and firing the powder-coated base at a temperature in a range of about 850° C. to 1000° C. to form the ceramic layer.

6. The process according to claim 5, wherein the recrystallized glass powder has a content of about 35% to 51% by weight $SiO_2$, about 25% to 38% by weight $Al_2O_3$ and about 10% to 39% by weight BaO.

7. The process according to claim 5, wherein the powder mixture is formed into a paste, which is applied by a screen printing process to the thermally-stable base.

8. The process according to claim 7, wherein the base on which the powder mixture or the paste containing the powder mixture is applied is a thermally-stable substrate or a functional layer on a thermally-stable substrate.

9. The process according to claim 8, wherein the thermally-stable substrate is a solid electrolyte having oxygen ion-conducting capacity.

* * * * *